United States Patent [19]

Lehmann

[11] 4,376,707
[45] Mar. 15, 1983

[54] PROCESS FOR THE REMOVAL OF UREA FROM BLOOD WASH FLUIDS AND BLOOD

[75] Inventor: Hans-Dieter Lehmann, Waltenhofen, Fed. Rep. of Germany

[73] Assignee: Gambro Dialysatoren G.m.b.H. & Co. K.G., Fed. Rep. of Germany

[21] Appl. No.: 243,968

[22] Filed: May 21, 1979

[51] Int. Cl.³ .............................................. B01D 15/00
[52] U.S. Cl. .................................... 210/679; 210/692; 210/927
[58] Field of Search ............... 210/638, 646, 647, 679, 210/692, 927

[56] References Cited

U.S. PATENT DOCUMENTS

| | | | |
|---|---|---|---|
| 3,525,686 | 8/1970 | Roberts | 210/22 |
| 3,560,380 | 2/1971 | Stade | 252/1 |
| 4,085,046 | 4/1978 | Saporito | 210/90 |
| 4,136,708 | 1/1979 | Cosentino et al. | 137/99 |

FOREIGN PATENT DOCUMENTS

| | | |
|---|---|---|
| 2305186 | 8/1973 | Fed. Rep. of Germany . |
| 1546072 | 11/1968 | France . |
| 2237639 | 2/1975 | France . |
| 2271864 | 12/1975 | France . |
| 2350864 | 12/1976 | France . |
| 2322155 | 3/1977 | France . |
| 288010 | 3/1965 | Netherlands . |
| 1368566 | 10/1974 | United Kingdom . |
| 1478971 | 7/1977 | United Kingdom . |

*Primary Examiner*—Ivars C. Cintins
*Attorney, Agent, or Firm*—Lerner, David, Littenberg & Samuel

[57] ABSTRACT

A process is disclosed for removing urea from blood wash fluids or blood fluids in which the fluids are treated with an organic solid containing at least one proton-containing secondary substituent group which masks and activates the aldehyde group and the fluids and the solid organic compound are separated.

9 Claims, No Drawings

PROCESS FOR THE REMOVAL OF UREA FROM BLOOD WASH FLUIDS AND BLOOD

BACKGROUND OF THE INVENTION

The invention relates to a dialysis or diafiltration method. More specifically, the invention relates to the treatment of blood wash fluids or blood fluids to remove urea. Patients suffering from kidney disorders are treated by so-called "blood washing" techniques in order to remove the urea from the blood, which is the largest constituent of the metabolic product of the human protein metabolism. This blood purification takes place by dialysis or diafiltration using semipermeable membranes. By the dialysis technique, the urea is filtered out of the blood through the membrane into a washing fluid; whereas in the diafiltration technique, blood fluids containing the dissolved urea, excluding proteins and blood corpuscles, filter through the membrane. The object of both methods is to obtain a closed circulatory system in which, in the dialysis method, the cleansing fluid is reused after removal of the urea, and with the diafiltration method, the blood fluid is reintroduced into the bloodstream after removal of the urea. A closed circulatory system of the cleansing fluid during dialysis is required to keep the size of the artificial kidneys small.

The pysiological conditions that must be observed when dealing with blood cleansing fluids or blood fluids make it a difficult task to eliminate urea from aqueous solutions. Several methods used to remove urea from cleansing fluid or blood fluids in a closed circulatory system have been investigated, but none has proved satisfactory so far.

An early attempt involved the removal of urea from the cleansing fluid of a dialyzer by using activated charcoal. At room temperature, however, activated carbon adsorbs only about 2 to 3 grams of urea per kilogram; whereas the body must excrete approximately 30 grams during one dialysis procedure. Therefore, about 10 to 15 kilograms of adsorption charcoal would be required. This large quantity, in turn, would require a large apparatus, and the advantages of a reduction of the size of the artificial kidney itself would be lost.

In another known procedure, urease is used to crack the urea enzymatically to ammonia, and the ammonium cations are then adsorbed in a cation exchanger. This procedure has the disadvantage that the pH and the electrolyte balance in the organism are disturbed by the ion exchange. Thus, if the procedure is carried out with blood fluids or recirculated blood cleansing fluid, an additional reinfusion of calcium, potassium, and magnesium ions is required. Furthermore, the sensitivity of the enzyme used for cracking the urea prohibits sterilization of the ion exchanger column. The fact that urease possesses a varying cracking quality, resulting in a non-reproducible cleansing efficiency, presents a further disadvantage.

Additional known procedures use oxystarch, oxycellulose or polyacrolein for conversion with urea. The disadvantage of this method is that these substances react with urea only relatively slowly under physiological conditions, thus requiring too much time for dialysis or diafiltration with a closed circulatory system. The use of oxypolysaccharides presents the problem of slow depolymerization.

Finally, oxidization of urea with nitrates or hypochlorites to remove urea from blood cleansing fluids was proposed. This method, however, presents the danger of the formation of carcinogenic nitrosamines or N-chloroamines.

Thus, it is highly desirable to create a procedure in which urea can be removed from blood cleansing fluids or blood fluids using a solid, which eliminates the above-mentioned disadvantages in the state of the art, achieves the most rapid and complete elimination of urea possible, keeps the amount of solid required for removal at a minimum, and finally, does not cause any reaction products hazardous to the organism.

SUMMARY OF THE INVENTION

It has now been discovered that these desirable characteristics can be obtained by a process in which blood wash fluids or blood fluids are treated with an organic solid containing at least one aldehyde group per molecule and at least one proton-containing secondary substituent group which masks and activates the aldehyde group and the fluids and organic solid are separated. The process is applicable in dialysis or diafiltration using semi-permeable membranes, and it results in rapid and extensive removal of urea, using a relatively small amount of the organic solid and without causing the formation of reaction products hazardous to the organism.

DETAILED DESCRIPTION OF THE INVENTION

Suitable secondary substituent groups are those exerting an electron attracting effect on adjoining groups, whereby the effect increases from the —$CONH_2$ group to the —COOH group and the —CHO group, becoming strongest with the —$SO_3H$ group. Examples of such secondary substituent groups are disclosed in "Lehrbuch der organischen Chemie," [Handbook of Organic Chemistry] by Klages, 1957, vol. II, pp. 323 ff., the disclosure of which is incorporated herein by reference.

Examples of suitable proton-containing secondary substituent groups in accordance with the present invention include the following groups: —COOH, —$CONH_2$, —$SO_3H$ and —$SO_2NH_2$. Preferred secondary substituent groups are —COOH, —CHO and —$SO_3H$, and most preferably, carboxyl groups and aldehyde groups.

Of course, in the compounds used according to the invention, the secondary substituent group can consist of various groups that fit into this category, and part of the substituent groups may also consist of primary substituent groups. Therefore it is sufficient for the preferred procedure using the carboxyl groups, for example, that the secondary substitutent groups consist at least partly of such carboxyl groups.

Compounds containing aldehyde groups, used according to the invention, may be aliphatic, cycloaliphatic, aromatic or heteroaromatic, and olefinic, aromatic and heteroaromatic compounds are preferred, since they favor the electron-attraction effect of the secondary substituent groups on the aldehyde group by the mesomerism or resonance effect of the double bonds. It is, therefore, advisable to use organic compounds in which the secondary substituent group is separate from an aldehyde group by a carbon-carbon bond or by an even number of carbon atoms that are connected by one or more conjugated double bonds.

Since the mesomeric or resonance effect decreases with the distance of the secondary substituent group from the aldehyde group, it is advisable that in the compound used, the secondary substituent group be separated from a neighboring aldehyde group by only two carbon atoms, which are connected by an olefinic double bond or which belong to an aromatic or heteroaromatic ring.

Examples of such compounds are glyoxylic acid, maleic aldehyde, and their derivatives, such as mucohalogenic acids, cyclic phenyls of maleic aldehyde and its derivatives, such as phthalaldehydic acid, o-phthalaldehyde and pyromellitic dialdehyde and their derivatives, as well as heterocyclic phenyls of maleic aldehydes such as nicotinic aldehyde and their derivatives. Preferred are phthalaldehydic acid and pyromellitic dialdehyde and their derivatives, especially phthalaldehydic acid. However, the compounds may be polymeric, containing several aldehyde groups in the molecule.

These compounds, in which the aldehyde group and the secondary substitute group, especially a carboxyl group or aldehyde group, are next to neighboring carbon atoms, mask the aldehyde group intramolecularly with the secondary substituent group by the formation of a hydroxylactone which is created by the addition of the proton-containing secondary substituent group to the aldehyde group and by the formation of a ring, especially a five-membered ring. For the phthalaldehydic acid of the following Formula I the hydroxylactone has the following Formula II:

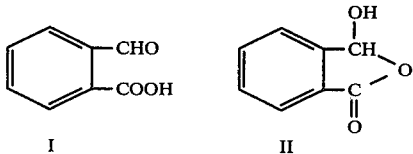

The masking of the aldehyde group by addition of the secondary substitute group does not necessarily have to occur intramolecularly, but may also occur intermolecularly if an intramolecular hydroxylactone formation would only be possible by the formation of ring systems which are unstable for steric reasons.

The simultaneous use of an acid, preferably a strong-acid cation exchanger, increases the effect of the compounds used according to the invention, containing at least one aldehyde group in the molecule. For example, a strong-acid cation exchanger based on divinylbenzene cross-linked polystyrene sulfonic acid may be used. It is advisable to use the acid cation exchanger in an amount from 0.01 to 10 g., preferably in an amount of 0.1 to 1 g. per gram of the organic compound with aldehyde groups. It is especially advisable to use the above-described compounds in a form fixed on a carrier, in order to contain them in a column through which the blood cleansing fluid or blood fluid can be directed for the removal of the urea. Fixation of these compounds on a carrier may be carried out on adsorbents such as, e.g., activated charcoal. If the compounds used acccording to the invention, with aldehyde groups and proton-containing secondary substituent groups, are polymeric themselves, e.g., vinyl polymers or polyphenylene oxide, no further fixation on a carrier is required.

Surprisingly, it has been found in accordance with the invention that compounds with aldehyde groups, which are activated and masked by a proton-containing secondary substituent groups, efficiently and completely eliminate urea from aqueous media such as dialysis fluid and diafiltrate under approximately physiological conditions. These compounds are at the same time selective against amino acids such as glycine. Furthermore, relatively small amounts are required, so that, in a closed circulatory system of dialysis fluid or blood fluid, the size of dialysis or diafiltration apparatus can be kept at a minimum. Of course, an amount of the organic solid effective to remove urea from the blood wash fluids or blood fluids is employed. Due to this surprising usefulness of such compounds with activated and masked aldehyde groups, the process according to the invention is especially well-suited for dialysis or diafiltration of human or animal blood or hemofiltrate.

The following examples are presented for purposes of demonstrating, but not limiting, the process of the invention.

EXAMPLE I

For fixation on a carrier of the compound o-phthalaldehydic acid (2-carboxybenzaldehyde), a solution of 10 g. o-phthalaldehydic acid in 2 l dialysis solution was pumped from a storage container through a column with adsorption charcoal which had been washed, dried and sterilized at 40° C. and at a velocity of 100 ml/min. in a circulatory system until no o-phthalaldehydic acid could be found in the storage solution.

At this point 4 g. urea were dissolved in the solution, which again was pumped through the column at 40° C. and at a speed of 100 ml/min.

The concentration of urea in the solution was measured. The initial concentration, corrected for volume, contained 244 mg % urea, and had decreased to 105 mg % after ½ hour. From that point on the concentration of urea decreased only slightly. After one hour it was 103.8 mg %, after 1½ hours it was 101.4 mg % and after 2 hours it was 95.5 mg %.

From this experiment it is evident that the amount of urea removed from the dialysis solution had already been removed for the most part after ½ hour, a fact that is contrary to known procedures for this purpose, which require several hours to produce a similar removal of urea.

EXAMPLE 2

In this example, four compounds according to the invention (A, D, E, F) were investigated together with three similarly structured compounds (C, G, H), not included in the substance of the invention, with respect to their usefulness in the removal of urea from aqueous electroytic solutions such as dialysis fluids, at a temperature of 40° C. The compounds investigated were the following:

A: 2-carboxybenzaldehyde (o-phtalaldehydic acid)
B: 2-carboxyacetophenone
C: 2-carboxybenzophenone
D: o-phthaldialdehyde
E: mucochloric acid
F: mucobromic acid
G: alpha-angelic actone
H: xanthydrol Since in some of the substances to be tested a balance exists between heterocyclic and open forms, i.e., free carbonic acid is present, the change in the pH value was tested, and an attempt was made to correct it by adsorption of the substance on active charcoal.

100 ml dialysis fluid (concentrate, diluted 1+34) was heated to 40° C. Stirring was continued for 10 minutes following the addition of 10 mMole reagent. A sample (a) was taken to measure pH value, then 10 mMole (=600 mg) urea was added, and the mixture was stirred for three hours at 40° C.

Another sample (b) was taken and the pH value measured immediately. Furthermore, after buffering with a phosphate buffer with a pH value of 6.6, the urea content was determined according to Berthelot.

20 g. dry activated charcoal was then added and the mixture was kept at 40° C. for two hours. After standing overnight at room temperature, the remaining solution (c) was again tested with respect to pH value and urea content. In cases of non-homogeneous reaction mixtures, the samples were centrifuged.

Results:

| Sample Reagent | a pH | a Appearance | b pH | Urea Content (mg %) | c pH |
|---|---|---|---|---|---|
| without | 7.6 | clear | 7.9 | 573 | 8.7 |
| A | 4.0 | slightly cloudy | 4.3 | 288* 279* | 6.3 |
| B | 3.7 | clear | 3.7 | 528 | 6.1 |
| C | 4.6 | partially undissolved | 4.7 | 554 | 5.8 |
| D | 7.2 | partially undissolved | 7.5 | 353* 354* | 7.9 |
| E | 3.7 | clear | 3.7 | 385 | 5.5 |
| F | 3.8 | clear | 3.8 | 439 | 5.4 |
| G | 6.2 | partially undissolved | 5.7 | 552 | 5.8 |
| H | 7.6 | hardly dissolved | 7.8 | 560 | 7.3 |

*double determination

From the table it is evident that the urea content in the solution had decreased noticeably only with the compounds used according to the invention 2-carboxybenzaldehyde (A) o-phthaldialdehyde (D) and the mucohalogenic acids (E, F). This decrease was higher for mucochloric acid (E) than for mucobromic acid (F). In the case of 2-carboxybenzaldehyde (A) the decrease was the most significant. The compounds with similar structures but not included in the substance of the invention, such as 2-carboxybenzophenone (C), angelic lactone (G) and xanthydrol (H), had no significant effect on the urea content of the solution.

The mixtures with A, E and F are acidic. In contrast to the mucohalogenic acids, the pH value in the mixture with 2-carboxybenzaldehyde (A) was increased significantly (to 6.3) by the addition of activated charcoal.

By using higher concentrations (10 mMole each) of reagent and urea in a mole ratio of 1:1 the urea concentration was reduced to approximately 50% by the reaction with 2-carboxybenzaldehyde.

EXAMPLE 3

The following adsorbents were added to a mixture of 0.9 g NaCl and 0.3 g urea in 100 ml water:
1. 0.5 g. acid cation exchanger LAB I+
2. 0.5 g LAB I+2.5 g activated charcoal (granulate)
3. 0.5 g LAB I+0.75 g phthalaldehydic acid
4. 0.5 g LAB I+1.5 g phthalaldehydic acid
5. 0.5 g LAB I+2.5 g activated charcoal +1.5 g phthalaldehydic acid
6. 0.5 g LAB I+3.0 g phthalaldehydic acid
7. 0.5 g LAB I+1.1 g pyromellitic dialdehyde
8. 0.5 g LAB I+2.2 g pyromellitic dialdehyde
9. 0.5 g LAB I+2.2 g pyromellitic dialdehyde +) LAB I strong-acid cation exchanger based on divinylbenzene cross-linked polystyrene sulfonic acid.

A sample was taken from the mixture, which was stirred at 40° C., after 1, 2, 3 and 4 hours. The sample was filtered and adjusted with phosphate buffer solution to pH 7.2. Then the urea content of the sample was determined according to Berthelot.

| Experiment No. | Initial Concentration | After 1 hr. | After 2 hrs | After 3 hrs | After 4 hrs |
|---|---|---|---|---|---|
| 1 | 300 | 286 | 297 | 288 | 292 |
| 2 | 300 | 261 | 266 | 264 | 264 |
| 3 | 300 | 225 | 191 | 168 | 111 |
| 4 | 300 | 160 | 105 | 84 | 59 |
| 5 | 300 | 172 | 145 | 132 | 122 |
| 6 | 300 | 55 | 32 | 26 | 26 |
| 7 | 300 | 243 | 185 | 170 | 149 |
| 8 | 300 | 77 | 43 | 53 | 61 |
| 9 | 300 | 98 | 88 | 100 | 90 |

It is evident from the results of the experiments that acid cation exchanger and activated charcoal do not produce any significant lowering of the urea content. In contrast, the compounds used according to the invention, phthalaldehydic acid and pyromellic dialdehyde, produce removal of up to more than 90% of the urea. It is especially striking that activated charcoal not only does not increase this technical effect of the compounds used according to the invention, but even causes it to decrease significantly, a fact which becomes apparent by comparing experiments 4 and 5, and experiments 8 and 9. This result is extremely surprising, since an additive effect would have been expected from the activated charcoal combined with the organic compounds used according to the invention.

EXAMPLE 4

The experiments were conducted as in Example 3, however, parallel to them, 100 ml of a 0.9% NaCl solution was employed each time, which contained 5 mMole of the amino acid glycine instead of the 5 mMole urea (equalling 0.3 g). After 4 hours samples were taken from the mixtures which had been stirred at 40° C., and their glycine content was determined photometrically by means of a ninhydrin reaction. The concentration of the initial solution with glycine was 392 mg %, that of the initial solution with urea was 300 mg %.

| | Glycine mg % after 4 hrs. | Urea mg % after 4 hrs |
|---|---|---|
| 1. 0.5 g LAB I (H+-form) control sample | 368 | 292 |
| 2. 0.5 g LAB I (H+-form) + 0.75 g phthalaldehydic acid | 318 | 111 |
| 3. 0.5 g LAB I (H+-form) + 1.5 g phthalaldehydic acid | 360 | 59 |
| 4. 0.5 g LAB I (H+-form) + 1.1 g pyromellitic dialdehyde | 350 | 149 |
| 5. 0.5 g LAB I (H+-form) + 2.2 g pyromellitic dialdehyde | 392 | 61 |

EXAMPLE 5

Fresh oxblood was adjusted with physiological common salt to a hematocrit of 25%. At a blood flow of 200 ml/min. and a difference in transmembrane pressure of 300 mm HG, 50 ml/min of protein-free hemofiltrate was filtered off through a polyamide membrane. 100 ml each of the mixture was mixed with 300 mg urea and stirred for 4 hours at 38° C. with the following adsorbents:
1. 1.5 g phthalaldehydic acid
2. 1.5 g phthalaldehydic acid +0.5 g strong-acid cation exchanger as in Example 3.

After 1, 2, 3 and 4 hours, the following urea contents were found:

| Experiment No. | Initial Concentration | After 1 hr. | After 2 hrs | After 3 hrs | After 4 hrs |
|---|---|---|---|---|---|
| 1 | 318 | 230 | 176 | — | 120 |
| 2 | 318 | 209.5 | 156 | 120 | 99 |

It will be understood that the embodiments described above are merely exemplary and that persons skilled in the art may make many variations and modifications without department from the spirit and scope of the invention. All such modifications and variations are intended to be included within the scope of the invention as defined by the appended claims.

What is claimed is:

1. A process for removing urea from blood wash fluid or blood fluid comprising the steps of treating said fluid with an organic solid containing at least one aldehyde group per molecule and at least one proton-containing secondary substituent group which masks and activates said aldehyde group to effect urea removal from said fluid, and separating said fluid from said organic solid.

2. A process according to claim 1, wherein said secondary substituent group is selected from the group consisting of —COOH, —CHO, —SO$_3$H, —CONH$_2$ and —SO$_2$NH$_2$.

3. A process according to claim 1, wherein said secondary substituent group is —COOH.

4. A process according to claim 1 or 2, wherein in said compound said secondary substituent group is separated from said aldehyde group by a carbon-carbon bond or an even number of carbon atoms containing at least one conjugated double bond.

5. A process according to claim 4, wherein in said compound said aldehyde group and said secondary substituent group are attached to adjacent carbon atoms, which carbon atoms are bonded together by an olefinic double bond, or are attached to adjacent carbon atoms of an aromatic or heteroaromatic ring.

6. A process according to claim 1, wherein said compound is selected from the group consisting of phthalaldehydic acid, o-phthaldialdehyde, pyromellitic dialdehyde and hydroxylactone derivatives thereof.

7. The process according to claim 1, wherein said compound is fixed on a carrier.

8. A process according to claim 7, wherein said carrier is activated carbon.

9. A process according to claim 1, wherein said fluids are treated with an acid cation exchanger in addition to the organic solid.

* * * * *